US 8,078,411 B2

(12) United States Patent
Ito et al.

(10) Patent No.: US 8,078,411 B2
(45) Date of Patent: *Dec. 13, 2011

(54) METHOD AND APPARATUS FOR CHROMATOGRAPHIC DATA PROCESSING

(75) Inventors: Masahito Ito, Hitachinaka (JP); Kisaburo Deguchi, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/611,181

(22) Filed: Nov. 3, 2009

(65) Prior Publication Data

US 2010/0057379 A1    Mar. 4, 2010

Related U.S. Application Data

(63) Continuation of application No. 12/155,812, filed on Jun. 10, 2008, now abandoned, which is a continuation of application No. 11/654,577, filed on Jan. 18, 2007, now Pat. No. 7,403,859, which is a continuation of application No. 11/061,610, filed on Feb. 22, 2005, now Pat. No. 7,200,494, which is a continuation of application No. 10/831,189, filed on Apr. 26, 2004, now Pat. No. 6,907,355, which is a continuation of application No. 09/959,575, filed as application No. PCT/JP99/05251 on Sep. 27, 1999, now Pat. No. 6,748,333.

(51) Int. Cl.
*G06F 19/00* (2006.01)
*G01N 31/00* (2006.01)

(52) U.S. Cl. .......................................... 702/32; 702/22

(58) Field of Classification Search .................... 702/22, 702/32, 76, 189, 194, 195
See application file for complete search history.

(56) References Cited

U.S. PATENT DOCUMENTS

| 4,807,148 A | 2/1989 | Lacey |
| 4,941,101 A | 7/1990 | Crilly |
| 5,277,871 A | 1/1994 | Fujii et al. |
| 5,291,426 A | 3/1994 | Collins et al. |
| 6,029,115 A | 2/2000 | Tracy et al. |
| 6,393,368 B1 | 5/2002 | Ito et al. |
| 6,529,836 B2 | 3/2003 | Ito et al. |
| 6,549,861 B1 | 4/2003 | Mark et al. |
| 6,815,668 B2 | 11/2004 | Miller et al. |

(Continued)

FOREIGN PATENT DOCUMENTS

JP    47-45556    11/1972

(Continued)

OTHER PUBLICATIONS

Goodman, K; Brenna, T., "Curve Fitting for Restoration of Accuracy for Overlapping Peaks in Gas Chromatography/Combustion Isotope Ratio Mas Spectrometry" Analytical Chemistry; vol. 66, No. 8; Apr. 1994; pp. 1204-1301.

(Continued)

*Primary Examiner* — John H Le
(74) *Attorney, Agent, or Firm* — Dickstein Shapiro LLP

(57) ABSTRACT

A chromatographic analyzer is provided for facilitating curve fitting by means of the linear least-square method for a chromatogram that contains a plurality of overlapping peaks. A chromatographic data processor executes fitting processing to each peak in an arbitrary time region having the plurality of peaks of the chromatogram starting from the front or back side of the time region or from the back side of the time region, and the processed peaks are subtracted from the chromatogram in the time region so that the plurality of peaks in the chromatogram can be separated from one another.

10 Claims, 7 Drawing Sheets

U.S. PATENT DOCUMENTS

| | | |
|---|---|---|
| 7,200,494 B2 | 4/2007 | Ito et al. |
| 7,403,859 B2 | 7/2008 | Ito et al. |

FOREIGN PATENT DOCUMENTS

| | | |
|---|---|---|
| JP | 49-113693 | 10/1974 |
| JP | 60-022659 | 2/1985 |
| JP | 62-85850 | 4/1987 |
| JP | 63-151851 | 6/1988 |
| JP | 6-324029 | 11/1994 |
| JP | 9-54071 | 2/1997 |
| JP | 9-503064 | 3/1997 |

OTHER PUBLICATIONS

Goodchild, S; Hurlbut, J; "A Compositional Heterogeneity Method to Simplify LC Data Anaysis"; American Labortaory; Issue 44; Sep. 1998.

Toft, J. et al., Non-Linear Curve Fitting of Bilinear Data Using Orthogonal Projections for Rank Analysis, Applications to Gas Chromatography/Infrared Specttrometry and Variable Temperature Infrared Studies; Vibrational Spectroscopy; vol. 7, No. 2; Jul. 1994; pp. 125-137.

NAME OF COMPONENT:Gly

| PARAMETER | FIT VALUE | UNCERTAINTY (DEVIATION) |
|---|---|---|
| PARAMETER $t_R$ (MIN) | 23.54 | 0.06 |
| PEAK AREA | 23,505 | 203 |
| STANDARD DEVIATION $\sigma$ | 0.199 | 0.005 |
| TAU $\tau$ (DISPLAY ONLY WHEN EMG IS USED) | 0.020 | 0.002 |

MEASURED VALUE (nmol):54.55 (UNCERTAINTY:0.47)

METHOD AND APPARATUS FOR CHROMATOGRAPHIC DATA PROCESSING

This application is a continuation of U.S. patent application Ser. No. 12/155,812, filed Jun. 10, 2008 now abandoned, which is a continuation of U.S. patent application Ser. No. 11/654,577, filed Jan. 18, 2007, now U.S. Pat. No. 7,403,859, which is a continuation of U.S. patent application Ser. No. 11/061,610, filed Feb. 22, 2005, now U.S. Pat. No. 7,200,494, which is a continuation of U.S. patent application Ser. No. 10/831,189, filed Apr. 26, 2004, now U.S. Pat. No. 6,907,355, which is a continuation of U.S. patent application Ser. No. 09/959,575, filed Oct. 30, 2001, now U.S. Pat. No. 6,748,333, which was the National Stage of International Application No. PCT/JP99/05251, filed Sep. 27, 1999, which are hereby incorporated by reference in their entirety.

TECHNICAL FIELD

The present invention relates to a chromatography technology such as a liquid chromatography technology, and particularly to a data processing method.

BACKGROUND ART

In chromatographs such as a liquid chromatographic analyzer, a gas chromatographic analyzer or the like, a sample to be measured is let to pass through a column to be separated into components, and each of the separated components is detected as an output value at each elapsing time using a photometer such as a chromatographic detector.

Signals output from the chromatographic detector are recorded as time sequential data having a time interval of several hundreds ms. This is what is called a chromatogram having signal intensity in the ordinate and retention time in abscissa. In general, the signal intensity is converted to a digital value $I_j$ every an arbitrary time interval (time $t_j$) to execute data processing.

FIG. 3 shows an example of a chromatogram obtained by executing a body fluid amino acid analysis.

As shown in FIG. 3, peaks of 11 components from Gly (glycine) to Tyr (tyrosine) densely exist in the range of retention time from 23 to 34 (min). In such a case, area-quantitative calculation is conventionally executed using a vertically dividing method in which a vertical line is drawn from each minimum point between peaks, that is, what is called "a root". However, this method produces an error as large as several tens % to cause an incorrect result when the peaks are strongly overlapped with each other. Therefore, when the chromatogram of such a kind needs to be quantitatively analyzed in a high accuracy, it has been general that the analyzing time is lengthened to improve the separation degree.

On the other hand, in order to perform quantitative calculation without lengthening the analyzing time even if peaks are overlapped so strongly with each other, quantitative calculation is tried to be performed using numerical analysis in a manner like data processing. This method is, for example, a non-linear least-square method.

In the case of using the non-linear least-square method, at least three independent parameters (A: area, $T_R$: retention time, $\sigma$: standard deviation) are used as variables in order to execute fitting of a peak for one component. Therefore, in order to execute fitting of peaks for a plurality of components, it is necessary to calculate three parameters of $A_i$, $T_{Ri}$, $\sigma_i$ for each of the components (i).

The conventional examples of using the non-linear least-square method are disclosed in Japanese Patent Application Laid-Open No. 6-324029 and Japanese Patent Application Laid-Open No. 63-151851.

These examples disclose that overlapping peaks on a chromatogram are curve-fit using a waveform function such as the Gaussian function or an EMG function (exponentially modified Gaussian function) which can express an asymmetric waveform of a peak. As shown in these examples, the overlapping peaks can be separated into individual peak waveforms, and the quantitative calculation can be performed by obtaining peak sizes such as a peak area and so on corresponding to a component of each of the peaks.

DISCLOSURE OF INVENTION

However, in the conventional examples using the non-linear least-square method, the separation of the peak waveforms is applied to two or three overlapping peaks, but not applied to of more than three overlapping peaks.

The reason is that in the case of separating the overlapping peak waveforms using curve fitting through the non-linear least-square method, as the number of peak components is increased to 3, 4, 5 . . . , there occurs a phenomenon that the fitting processing is difficult to be converged or that the separation of peaks can not correctly performed (the error is increased).

For example, in the case of the chromatogram shown in FIG. 3, when fitting is tried to the 11 components from Gly to Tyr at a time, the 33 parameters of 11×3 must be determined at a time. This is very difficult calculation processing to the non-linear least-square method, and accordingly various kinds of techniques are necessary in order to solve this problem. Therefore, when the curve-fitting is executed using the non-linear least-square method in the case of existing many overlapping peaks on a chromatogram, a measuring operator must specify calculation regions (time windows) for 2 or 3 peaks seeming to be converged one by one. This process expenses much time and much effort, and in addition, there is a problem in the reliability of the calculation result because the regions are artificially determined.

An object of the present invention is to provide a chromatographic analyzer capable of easily executing curve fitting using the non-linear least-square method to a chromatogram having a plurality of overlapping peaks.

The present invention to attain the above object is characterized by a chromatographic data processor for executing data processing of a chromatogram obtained by separating a sample to be measured using a column and detecting the separated sample, wherein fitting processing is executed to each peak in an arbitrary time region having the plurality of peaks of the chromatogram starting from the front side of the time region or from the back side of the time region, and the processed peaks are subtracted from the time region of the chromatogram so that the plurality of peaks in the chromatogram can be separated from one another.

The object, the operation and the effect of the present invention will be described in detail in the section of DESCRIPTION OF THE PREFERRED EMBODIMENTS to be described later.

BEST MODE IN WHICH THE INVENTION IS CARRIED OUT

An embodiment of the present invention will be described below.

Figure 2:
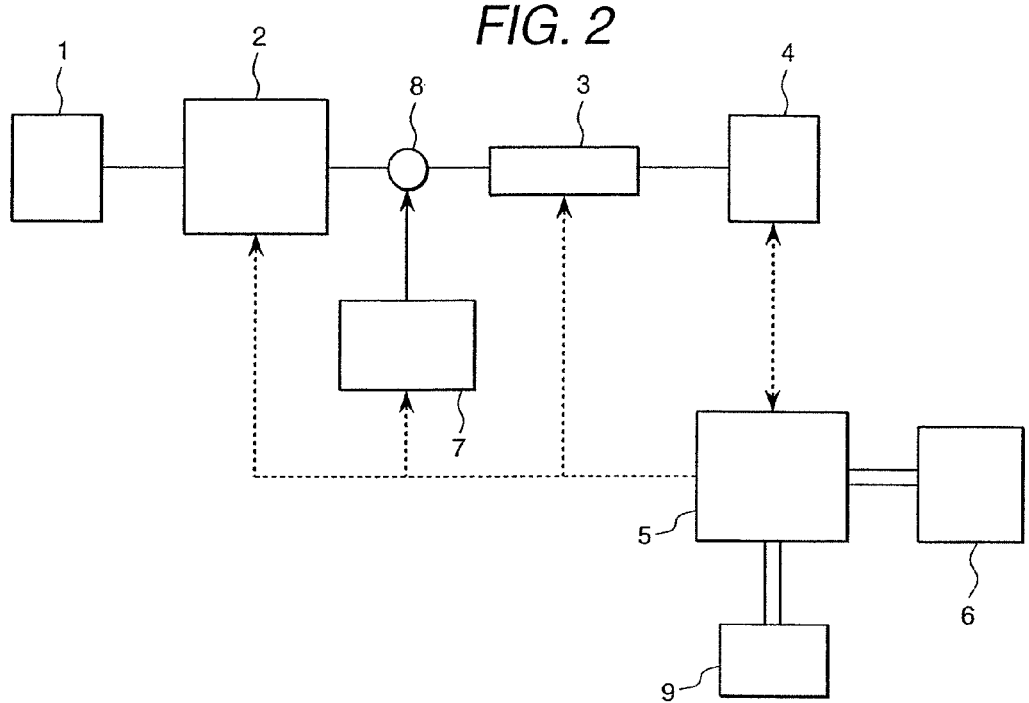
FIG. 2 is a diagram showing the outline of a chromatographic analyzer.

FIG. 2 is a diagram showing the outline of a liquid chromatographic analyzer to which the present invention is applied. An eluting solution 1 is initially pumped to a column 3 using a fluid pump 2 by an instruction from a controller 5. A sample supply portion 8 is arranged between the fluid pump 2 and the column 3, and a sample is supplied from a sampler 7 containing the sample to the eluting solution by an instruction of the controller 5. The sample is separated by the column 3 to be detected using a detector 4 such as a UV detector. A chromatogram of the detected data is transmitted to the controller 5 to be data-analyzed, and the result is displayed on a display 6 or printed by a Printer 9.

Figure 3:
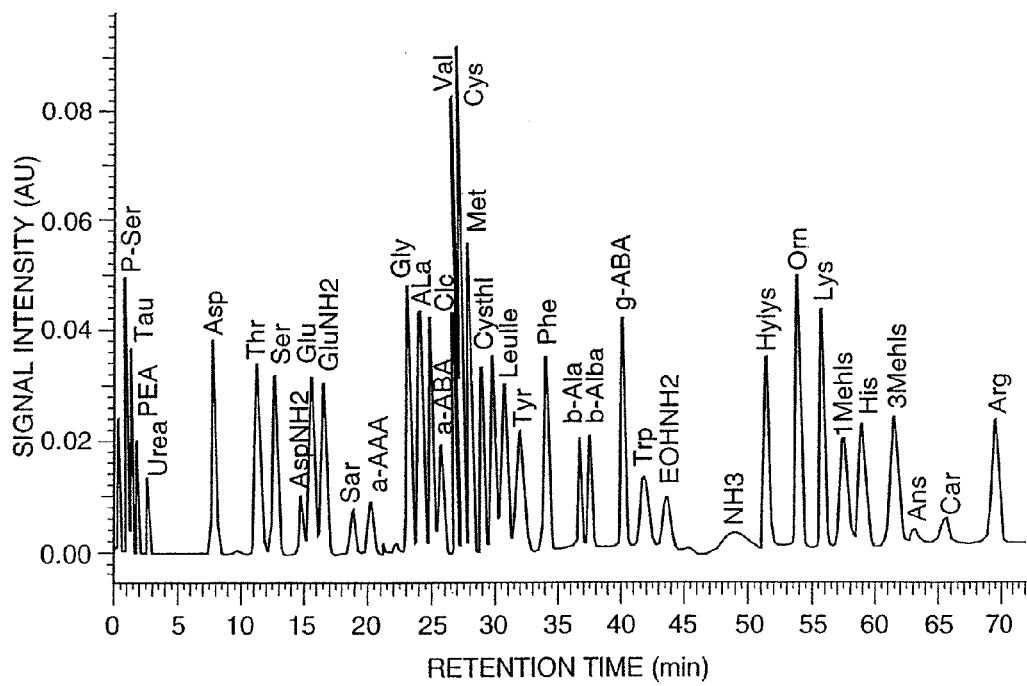
FIG. 3 is a chart showing a chromatogram for 70 minutes of a body fluid amino acid analysis method.

Data processing in the controller 5 will be described below when the chromatogram of FIG. 3 is obtained as the detected result.

In the present embodiment, the data processing of the chromatogram is executed mainly according to the following procedure.

Step 1: specification of a time interval to execute fitting thereto.
Step 2: selection of a weighting pattern.
Step 3: selection of a fitting direction.
Step 4: clicking of a fitting execution button.
Step 5: displaying and outputting of the result.

Figure 1:
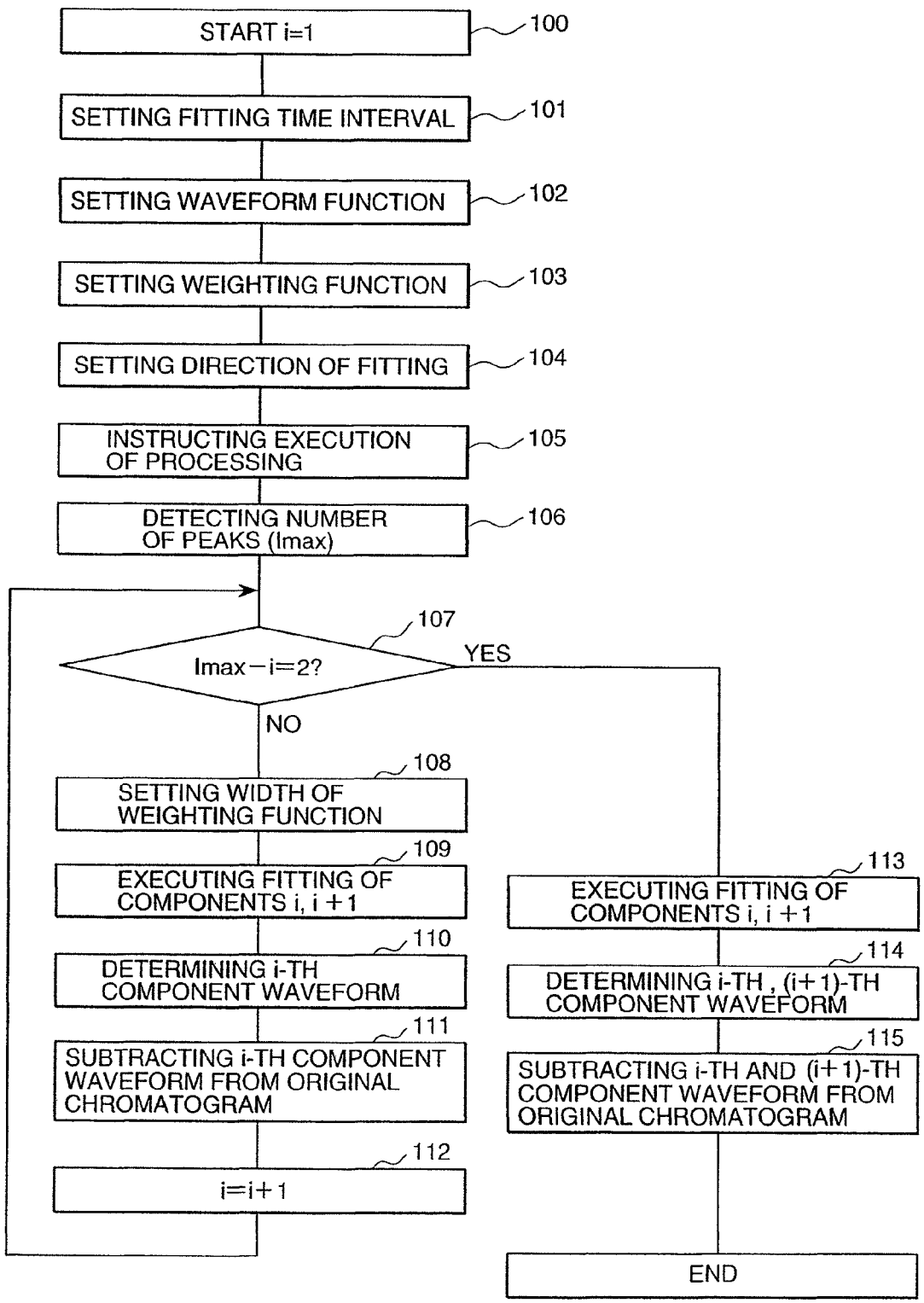
FIG. 1 is a flowchart showing fitting processing in accordance with the present invention.

FIG. 1 is a flowchart showing the detailed process of the data processing of the chromatogram described above. In the present embodiment, description will be made on a case where the fitting processing is executed two components by two components.

Initially, a chromatogram to be executed fitting is selected from detected results obtained to start the processing (100). Here, the variable i is set to 1 (one), that is i=1.

Figure 4:
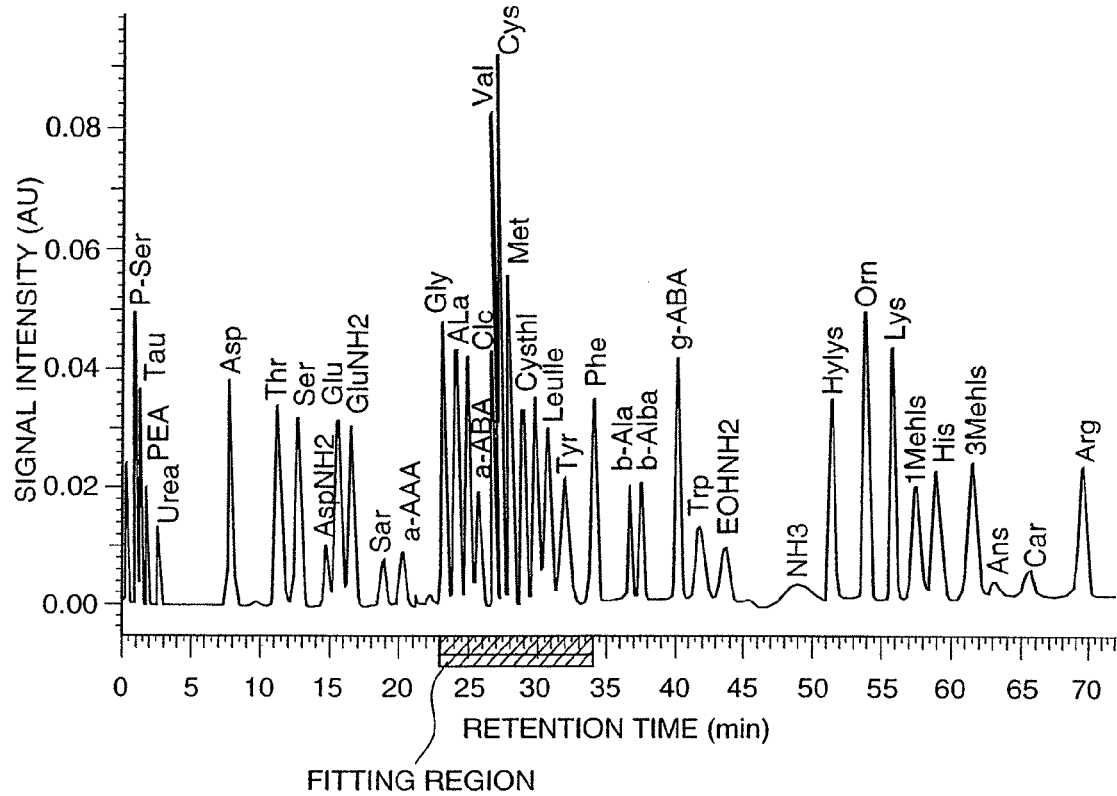
FIG. 4 is a chart showing an example of a display of a chromatogram in which a time window is set.

Next, an interval of retention time to execute fitting processing thereto (a time window) is set (101). Here, the peak group of 11 components from Gly to Tyr in the chromatogram of FIG. 4 is set to the time window.

The setting of time window is performed by dragging the time abscissa of the chromatogram displayed on the display 9 using a cursor. Otherwise, a peak starting and a peak ending the fitting may be selected by picking the peaks Gly and Tyr of the chromatogram displayed. Further, it is possible to employ a method of inputting a starting time and an ending time.

Figure 5:
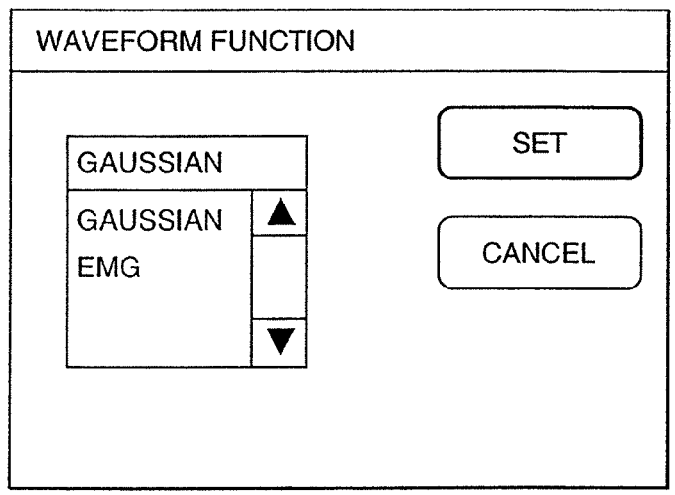
FIG. 5 is a view showing an example of a display of a dialogue box for setting a waveform function.

Next, a waveform function used for the fitting calculation is set. As the waveform function, for example, "Gaussian" or "EMG" may be selected. This selection can be performed by selecting a waveform function used using a dialogue box on the display 9 shown in FIG. 5.

Although the fitting in the present embodiment is executed two components by two components, it is necessary to make the influence of signals of a second and later waveforms in order to accurately determine a waveform of a peak in the front side of the fitting direction, that is, a first peak. Therefore, a weighting function shown in FIG. 6 (a) is set (103).

The weighting function is a function for weighting each of the two peaks. The example of FIG. 6(a) is a function that the weight w is set to 1 (one), that is, w=1 from a peak start time 21 to a peak end (root) time 23 of the first peak, and then the weight w is linearly slanted to be reduced from 1 to 0 from a peak start time 23 to a peak end (root) time 25 of the second peak. As the weighting function, various kinds of weighting functions may be employed. Some of the examples are described below.

FIG. 6(b): a weighting function having a curvilinear gradient. FIG. 6(c): a weighting function having an S-shaped curvilinear gradient. FIG. 6(d): a weighting function having a linear gradient from a peak start point of a first peak to a peak end point of a second peak. FIG. 6(e): a weighting function having a weight of 0.5 at an end point of a second peak. FIG. 6(f): a weighting function having a linear gradient from a maximum point of a second peak to an end point of the second peak. FIG. 6(g): a weighting function having a linear gradient from a maximum point of a first peak to an end point of a second peak by particularly attaching importance to the left-hand side of the first peak. The weight of 0.5 is set to an end point of the first, peak (a start point of the second peak. FIG. 6(h): a weight function having a flat weight of 0.5 from an end point of a first peak (a start point of a second peak) to an end point of the second peak. FIG. 6(i): a weighting function which is equivalent to a case without any weight.

Figure 6:
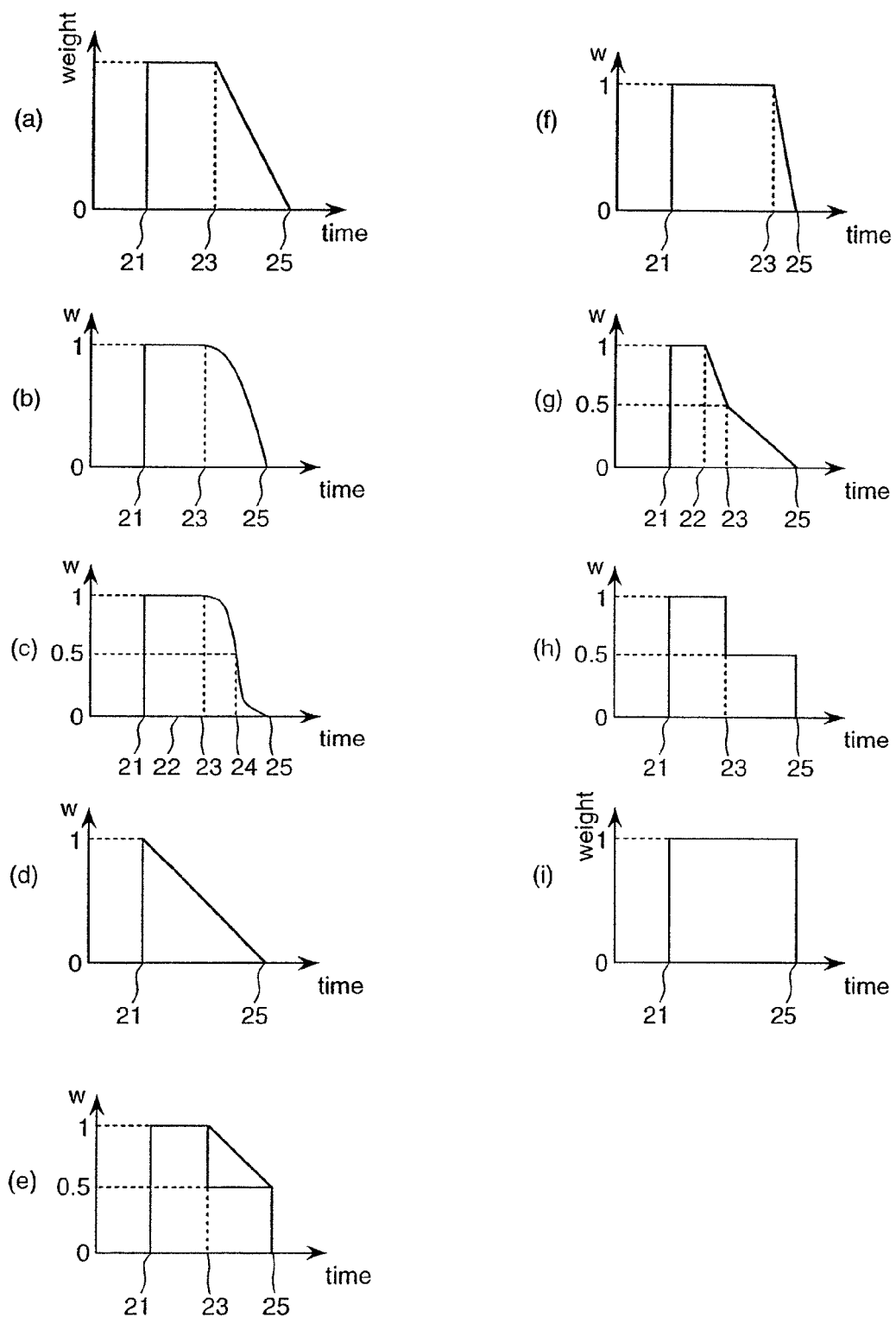
FIG. 6 is diagrams showing examples of weighting functions.
Figure 7:
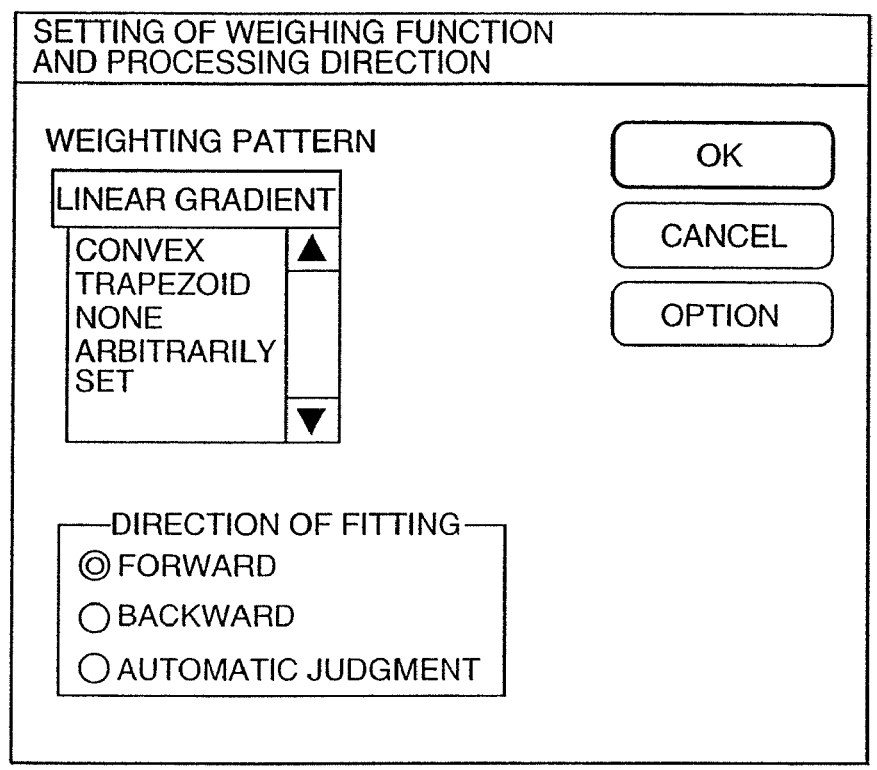
FIG. 7 is a view showing an example of a display of a dialogue box for selecting a weighting function and a direction of fitting.

In the concrete, the weighting function is set by displaying a dialogue box shown in FIG. 7 on the display 9 and selecting a weighting pattern. Therein, by selecting an "ARBITRARY SET" and pushing an "OPTION" button, the above-described various kinds of pattern function type graphs shown in FIG. 6 can be set. The various kinds of patterns of FIG. 6 are pre-stored in a memory such as a hard disk in the controller 5, and can be easily read out from the memory to be used for the processing by being specified using a dialogue box of FIG. 7.

Next, a direction of executing fitting calculation is determined (104).

That is, describing the example of FIG. 3, it is decided whether the processing is executed from the front side (the Gly side) or the back side (the Tyr side). In the concrete, the setting of the direction executing the fitting calculation is set using the dialogue box shown in FIG. 7.

An example of executing the processing from the Gly side will be described below.

By the above, setting of the conditions necessary for the fitting processing has been completed.

Figure 8:
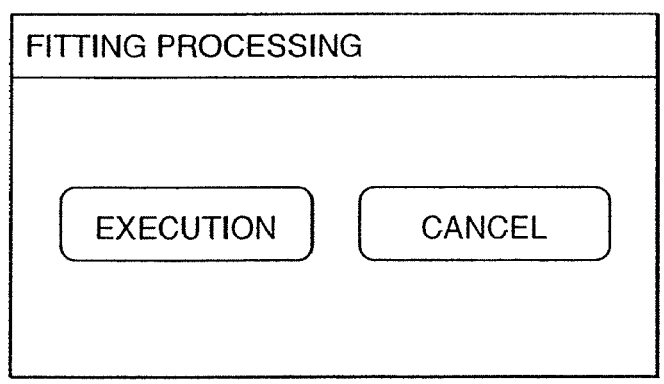
FIG. 8 is a view showing a dialogue box for instructing execution of the fitting processing.

Then, a dialogue box shown in FIG. 8 is displayed after selecting an "OK" button in the dialogue box of FIG. 7, and the fitting calculation processing is started by pushing an "EXECUTION" button.

As the calculation processing is started, number of peaks within the set time window is detected to be set to Imax (106).

In the concrete, inflection points inside the set time window are detected to obtain maximum points and minimum points, and an interval for each of the peaks is defined by determining the maximum point as the apex and the minimum points as the end point and the starting point of the peak. Therein, the roots (the minimum points) of the peak and a retention time having the points are stored in relation to each other.

Next, a difference between Imax and i is calculated (107). Therein, if the difference is larger than 3 (three components), the processing proceeds to Process 108.

When it is judged in Process 107 that the difference is larger than 3 (three components), a width of the weighting function set in Process 103 is adjusted so as to meet with a width between the roots detected in Process 105 (108).

Figure 9:
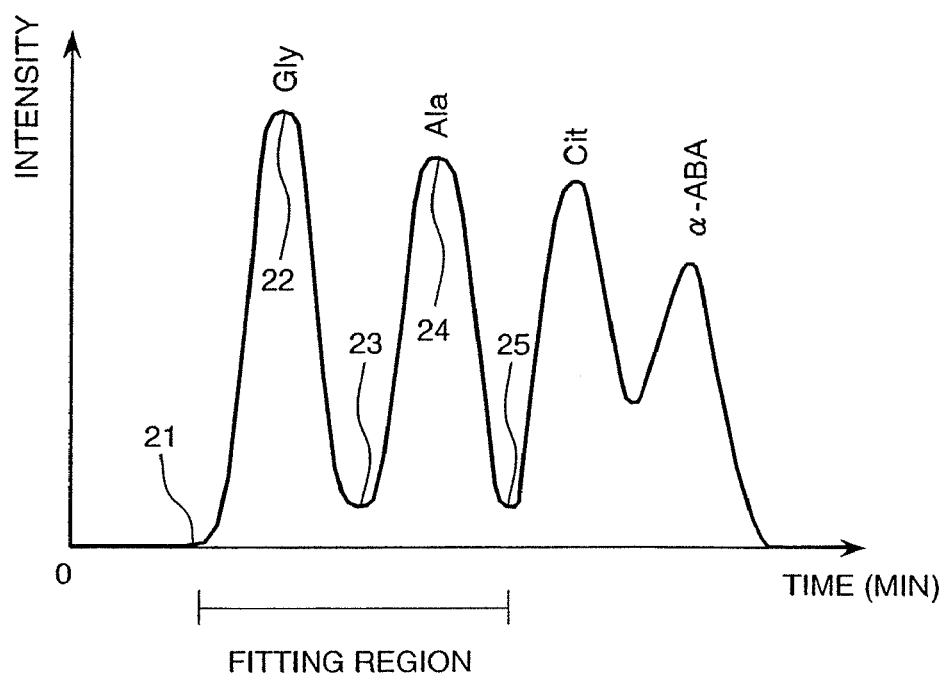
FIG. 9 is an illustrating chart showing a chromatogram in which a first fitting region is set.

FIG. 9 is an illustrating chart showing a chromatogram in which a region of first fitting processing is set. The width of the weighting function is adjusted so as to meet with the width of the fitting region as shown in FIG. 9.

Next, the fitting processing is executed to the two components of the front side in the fitting direction (109).

The fitting processing will be described below in detail.

As described above, the Gaussian or EMG function is used as the waveform function f(t) for the fitting. Firstly, in a case of employing the Gaussian function, the waveform function is shown in Equation 1.

$$f(t) = g_1(t) + g_2(t) + at + b \quad \text{(Equation 1)}$$
$$= \frac{A_1}{\sqrt{2\pi}\,\sigma_1} \exp\left\{-\frac{(t-t_{R1})^2}{2\sigma_1^2}\right\} + \frac{A_2}{\sqrt{2\pi}\,\sigma_2}$$
$$\exp\left\{-\frac{(t-t_{R2})^2}{2\sigma_2^2}\right\} + at + b$$

($g_i(t)$: the suffix $i$ denotes a component $i$.)

There, the term (at+b) denotes a base line. Though the waveform function becomes Equation 1 shown above because the fitting processing is executed two components by two components in the present embodiment, the fitting processing may be executed three components by three components if the capability of non-linear least-square method can be secured. Of course, extension to the EMG function may be possible. In a case of employing the EMG function, the term $g_i(t)$ of the waveform function in Equation 1 is replaced by Equation 2.

$$g_1^{EMG}(t) = \frac{A_i}{\sqrt{2\pi}\,\sigma_i\tau_i}\int_0^t \exp\left\{-\frac{(t-t_{Ri}-t')^2}{2\sigma_i^2} - \frac{t'}{\tau_i}\right\}dt' \quad \text{(Equation 2)}$$

In the least-square method, each of the fitting parameters $A_i$, $t_{Ri}$, $\sigma_i$ and $\tau_i$ is determined so as to minimize the following $S_1$ of Equation 3 or the following $S_2$ of Equation 4. There, $I_j$ is a signal intensity of a measured chromatogram, j is a suffix expressing time $t_j$, and N is number of data points in a time interval. Either of $S_1$ and $S_2$ may be used.

$$S_1 = \sum_{j=1}^{N} w_j(f(t_j) - I_j)^2 \quad \text{(Equation 3)}$$

$$S_2 = \sum_{j=1}^{N} w_j^2(f(t_j) - I_j)^2 \quad \text{(Equation 4)}$$

The function $g_i(t)$ having a smaller value of $t_R$ (that is, the earlier retention time) in the f(t) of Equation 1 obtained here corresponds to the first peak Gly, and accordingly the waveform of the first component is determined (110).

Figure 10:
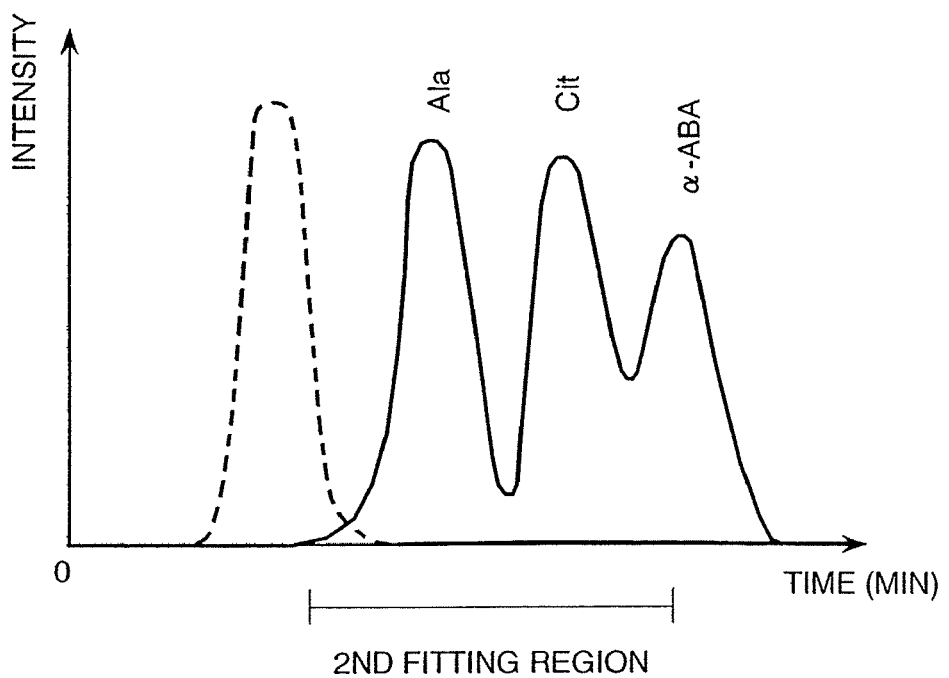
FIG. 10 is an illustrating chart showing the chromatogram in which a first component is cut out.

Next, the waveform of the first component $g_i(t)$ is subtracted from the original measured chromatogram to form a chromatogram cut out the first peak Gly (111). FIG. 10 is an illustrating chart showing the chromatogram in which the first peak Gly has been cut out. It is preferable not to subtract the base line at+b from the original chromatogram because it does not influence the peak waveform.

Next, the variable i is incremented, and the processing is returned to Process 107.

Then, the fitting processing for the peaks Ala and Cit is executed to determine the second component waveform of the second peak Ala according to the same procedure as that of the fitting processing for the first peak.

After that, the peaks Ala, Cit . . . are successively subtracted until the peaks for two components Leu (leucine) and Tyr in the back side end. When the remaining becomes two components (i=2), the processing proceeds to Process 113 to determine the peak waveforms of the final two components by executing the peak fitting for the two components without weighting (114). Then, the peak waveforms for the two components are subtracted from the original chromatogram (115) to complete the processing.

By the series of the processing described above, all the waveforms in the time window have been separated from one another. Further, according to the above-described processing, since the remaining chromatogram after cutting out all the peak waveforms becomes a base line, the base line can be obtained at a time.

Figures 11, 12:
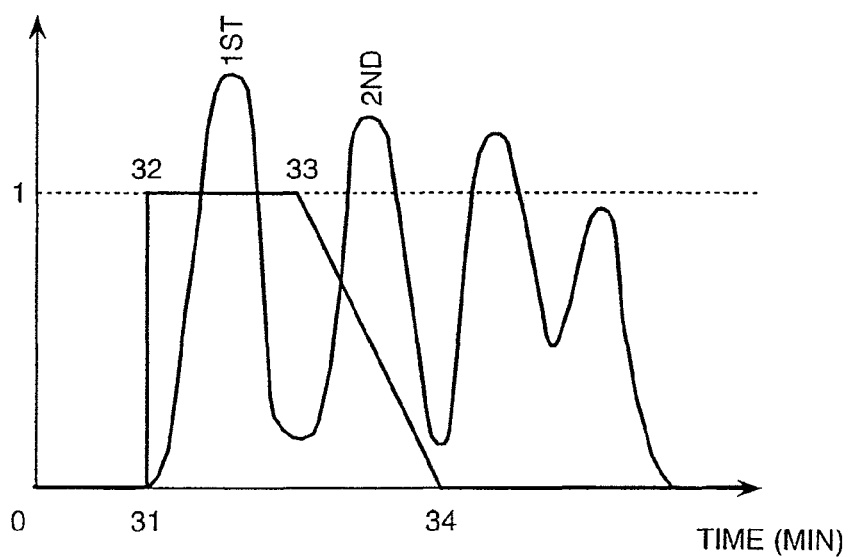
FIG. 11 is a view showing an example of a display of a fitting result.
FIG. 12 is a chart showing an example of graphically setting the weighting function.

After completion of the above-described processing, quantitative calculation (for example, concentration) is executed using parameters for each of the peaks obtained by the above-described processing. Then, a display for each of the peaks (each of the components) shown in FIG. 11 is displayed on the display 9 as the calculation result.

There, because the uncertainties (deviations) of the parameters for each of the components can be obtained by the above-described processing, the uncertainty of each of the measured quantitative values can be calculated based on the above-described uncertainties.

The point that the uncertainties of the measured quantitative values can be calculated is also one of the advantages of the present embodiment the calculation of obtaining the uncertainties of the measured quantitative values is executed according to the error propagation equation.

Further, the quality of the fitting can be judged from the magnitude of the uncertainty of the measured quantitative value (it can be said that the quality is better when the uncertainty is smaller). For example, the uncertainty can be used for judging quality of the calculation result of the overlapping portion when the fitting processing executed from both of the front side end and the back side end which is to be described later.

In the present invention, the above-described processing executing separating the peaks while the peaks are successively being cutting out is called as "sequencing", and the chromatographic data processor for executing the sequencing is called as "a chromatographic peak sequencer".

Although the fitting calculation described above is executed from the front side end, the fitting calculation may be executed from the back side end by setting the fitting direction of the dialogue box of FIG. 7. In this case, the function $g_2(t)$ expressing the second peak is subtracted from the chromatogram, and the shape of the weighting function is reversed left to right. In the processing direction described above, the peaks are cut out from the peaks having the larger retention time, that is, in order of the peaks Tyr, Leu, Ile (isoleucine) in the case of FIG. 4.

Ideally, the fitting processing may be executed from either of the front side and the back side. However, actually, it is preferable that the fitting processing is executed from the both sides toward a peak having the strongest overlapping intensity. When such fitting processing is performed, the button "AUTOMATIC JUDGMENT" in the dialogue box of FIG. 7 is selected.

For example, in the case of the chromatogram of FIG. 3, the forward sequencing processing is executed from the peak Gly to the peak Cysthi (Cystathionine) or Ile and the backward sequencing processing is executed to the peak Lue or Ile because overlapping of the peaks Lue and Ile is strong. By doing so, in regard to the peaks Lue and Ile, which fitting result should be employed and determined can be judged by comparing the appropriateness of the fitting results between the forward processing and the backward processing.

Therein, the judgment can be executed by using the uncertainties (the deviations) of the fitting parameters $A_i$, $t_{Ri}$ and $\sigma_i$ themselves as the indexes for judging the appropriateness or by using the statistical index $\chi_2$ or number of repetitive calculating times for watching the convergence rate of $\chi_2$. Further, more comprehensive judgment can be performed by combining these parameters. Any way, the peak area value $A_i$ needs to be accurately calculated in to execute quantitative value calculation, and accordingly importance should be placed on the uncertainty of the peak area value $A_i$.

Another Embodiment of Setting the Weighting Function

Although the weighting function set in the above-described process 102 has been set on the dialogue box, the weighting function may be set through a program setting method in which a table method shown in Table 1 is used or through a graphical setting method in which setting is performed by displaying and superposing the weighting function on a chromatogram as shown in FIG. 12.

TABLE 1

Weighting program (expressing FIG. 6 (g))

| Characteristic point | Weighting value | Shape |
|---|---|---|
|  | 0 |  |
| starting point of first peak | 1 | drawing a vertical line |
|  |  | horizontal line |
| apex of first peak | 1 |  |
|  |  | gradient (straight line) |
| root between peaks | 0.5 |  |
|  |  | gradient (convex) |
| end point of second peak | 0 |  |

The setting program of Table 1 shows the example of setting the weighting function of FIG. 6(g). The weighting function is defined by that a measurer inputs "weighting values" and "shapes". Table 1 is displayed on the display.

FIG. 12 shows the method of setting the weighting function by superposing on the chromatogram on the display. For example, a cursor is moved to a point near a node 31 using a pointing device, and a characteristic point of the first peak starting point is displayed by clicking on the point. By doing so, the node 31 is determined. When the node 31 needs to be moved, the node is picked and then released. That is, the node may be dragged. Next, a node 32 is determined by clicking on a point near the node 32 and vertically dragging the node 31 to a point having a weight of 1. Therein, a vertical line is automatically drawn from the node 31 to the node 32 and determined. Similarly, nodes 33 and 34 are determined to set the weighting function. When the weighting function needs to be changed, changing of setting can be performed by clicking an arbitrary node to highlight the node. Further, a node can be deleted. Furthermore, a new node can be added by clicking an arbitrary point. When a line section between nodes is changed to a curvilinear line, the line section to be changed is clicked to be highlighted (the displaying color is changed), and the set attribution is changed by light-hand side clicking. Therein, concave, convex or the like can be specified.

Another Embodiment of Sequencing

In the embodiment of sequencing described above, the measurement is once performed to obtain a chromatogram, and after that the data processing is performed. However, it is possible to simultaneously execute the sequencing processing with measuring of the sample. An embodiment in such a case will be described below.

The simultaneous sequencing processing with measurement is progressed as follows.

Step 1: setting of a time interval (a time window) to execute fitting thereto.
Step 2: setting of a weighting pattern.
Step 3: setting of a fitting direction.
Step 4: measuring of a sample.
Step 5: executing of fitting processing.
Step 6: displaying and outputting of the result.

In Steps 1 to 3, a time program is set before starting measurement as shown in Table 2. A time window is set by specifying a time period from the fitting start time to the fitting end time. In addition, the time window may be also set by selecting a fitting start peak and a fitting end peak as by specifying peak names "Gly" to "Tyr".

TABLE 2

Time Program

| Time | Command | Status |
|---|---|---|
| 0.0 | Waveform function | Gaussian |
| 0.0 | Weighting function | Straight line gradient |
| 0.0 | Fitting direction | Automatic judgment |
| 23.0 | Fitting start | ON |
| 34.0 | Fitting end | ON |

According to the chromatographic peak sequencer in accordance with the present invention, fitting of a chromatogram having a plurality of overlapping peaks can be automatically executed only by setting some number of conditions.

Further, a highly accurate base line can be calculate at the same time. From the viewpoint of existing the highly accurate base line determining function, the chromatographic peak sequencer in accordance with the present invention is considered to be an excellent data processor. However, because the fitting is executed by assuming the shape of peak waveform as a shape of Gaussian or EMG function, an attention should be paid on this point when a shape of an actual peak waveform is significantly different from the shapes of these analytical functions. In such a case, it is necessary to pre-store specific waveform functions by obtaining an isolated peak waveform for each component from a standard sample.

According to the present invention, in a chromatogram having a plurality of overlapping peaks, particularly, having three or more overlapping peaks, the peaks can be easily separated only by setting some number of setting conditions. By doing so, the accuracy of quantitative analysis and qualitative analysis can be improved. Further, the capability of determining the base line can be also improved. Furthermore, measurer's labor for the data processing can be substantially reduced.

What is claimed is:

1. A chromatographic analyzer comprising:
a sample separating unit for separating a sample to be measured into components;
a detecting unit for detecting the separated sample, the detecting unit comprising a photometer capable of detecting each of the components as an output value at each elapsing time;
a data processing unit for executing data processing by obtaining a detected result from the detecting unit, the data processing unit comprising: a unit which specifies a retention time interval having a plurality of peaks of a chromatogram obtained as the detected result of the detecting unit; and a unit which specifies a fitting direction for executing fitting processing in the specified fitting direction for the specified retention time interval; and
a display unit for displaying a dialogue box for selecting the fitting direction and for displaying a fitting result obtained from the data processing unit.

2. The chromatographic analyzer of claim 1, wherein, when a forward sequencing processing is selected as the fitting direction, the data processing unit executes fitting processing to obtain a fitting result from a front side end of the retention time interval.

3. The chromatographic analyzer of claim 1, wherein, when a backward sequencing processing is selected as the fitting direction, the data processing unit executes fitting processing to obtain a fitting result from a back side end of the retention time interval.

4. The chromatographic analyzer of claim 1, wherein, when a forward and backward sequencing processing is selected as the fitting direction, the data processing unit executes fitting processing to obtain fitting results from both a front side end and a back side end of the retention time interval.

5. The chromatographic analyzer of claim 4, wherein the data processing unit compares the fitting results obtained from the front side and the back side of the retention time interval and determines a fitting result for display based on the comparison.

6. The chromatographic analyzer of claim 4, wherein the data processing unit calculates an uncertainty value for each parameter of a respective fitting result and selects a fitting result for display based on the uncertainty value.

7. A chromatographic analyzer comprising:
a sample separating unit which separates a sample to be measured into components;
a detecting unit which detects the separated sample, the detecting unit comprising a photometer capable of detecting each of the components as an output value at each elapsing time;
a data processing unit which executes data processing by obtaining a detected result from the detecting unit, the data processing unit comprising a unit which specifies a fitting region having a plurality of peaks of a chromatogram obtained as the detected result of the detecting unit, wherein the fitting region represents an interval of retention time for executing fitting processing; and
a display unit for displaying means for specifying a starting value and an ending value for the fitting region and for displaying results obtained from the data processing unit.

8. The chromatographic analyzer of claim 7, wherein specifying the starting value and the ending value of the fitting region comprises dragging a time abscissa of the displayed chromatogram.

9. The chromatographic analyzer of claim 7, wherein specifying the starting value and the ending value of the fitting region comprises selecting a first peak from the displayed chromatogram as the starting value and selecting a second peak from the displayed chromatogram as the ending value.

10. The chromatographic analyzer of claim 7, wherein specifying the starting value and the ending value of the fitting region comprises inputting the starting value and the ending value using a dialogue box.

* * * * *